United States Patent [19]
DuRoss

[11] Patent Number: 5,139,795
[45] Date of Patent: Aug. 18, 1992

[54] MELT CRYSTALLIZED XYLITOL

[75] Inventor: James W. DuRoss, Smryna, Del.

[73] Assignee: ICI Americas Inc., Wilmington, Del.

[21] Appl. No.: 743,487

[22] Filed: Aug. 9, 1991

[51] Int. Cl.$^5$ .................. A23G 3/30; A23L 1/09; A23P 1/02
[52] U.S. Cl. .................. 426/3; 426/454; 426/658; 426/660; 127/29; 568/868
[58] Field of Search .............. 426/658, 454, 660, 96; 127/29; 536/4.1, 18.6; 568/863, 852, 868

[56] References Cited

U.S. PATENT DOCUMENTS

| | | | |
|---|---|---|---|
| 3,558,725 | 1/1971 | Kohno et al. | 260/635 |
| 3,985,815 | 10/1976 | Jaffe et al. | 260/637 |
| 4,086,371 | 4/1978 | Minifie et al. | 426/658 |
| 4,362,757 | 12/1982 | Chen | 426/658 |
| 4,886,677 | 12/1989 | Kondou | 426/658 |
| 4,999,058 | 3/1991 | Kawashima et al. | 426/658 |
| 5,023,092 | 6/1991 | DuRoss | 426/3 |
| 5,045,340 | 9/1991 | Kohler | 426/658 |

OTHER PUBLICATIONS

Waler et al, "The effect of Xylitolon Plaque Metabolism" Swedish Dental Journal, vol. 8, Issue 3, pp. 155-161 (1984).

Primary Examiner—Jeanette Hunter

[57] ABSTRACT

Melt crystallized xylitol possesses an agglomerated crystalline structure under a scanning electron microscope; an increased surface area relative to aqueous crystallized xylitol, of at least about 0.12 square meters per gram; and unexpected hardness values when compressed into a tablet. Chewing gum compositions comprising such melt crystallized xylitol are much less tacky and gritty compared to gum compositions comprising equal proportions of conventional aqueous crystallized xylitol of similar particle size distribution.

8 Claims, 2 Drawing Sheets

MELT CRYSTALLIZED XYLITOL

FIELD OF THE INVENTION

This invention relates to a novel form of crystalline xylitol characterized by a porous agglomerated crystalline structure when viewed under a scanning electron microscope; an increased surface area relative to aqueous crystallized xylitol of at least about 0.12 square meters per gram; and the ability to be directly compressed into a tablet having a desirable hardness when ground. In another aspect, this invention is directed to a process for the production of such novel form of xylitol, which process involves the melt crystallization of molten material.

BACKGROUND OF THE INVENTION

Traditionally, xylitol has been produced by the crystallization of a saturated aequeous solution of xylitol to form single crystals, tetrahedron in shape, of relatively uniform size. These crystals are grown in solution, separated from solution by centrifuging, drying the crystals and then grinding them into a powder. Thus, for example, Kirk-Othmer, Encyclopedia of Chemical Technology, Third Ed., (1978), John Wiley & Sons, indicate (at Vol. I, page 766) that "Xylose is obtained from sulfite liquors, particularly from hardwoods, such as birch, by methanol extraction of concentrates or dried sulfite lyes, ultrafiltration and reverse osmosis, ion exchange, ion exclusion, or combinations of these treatments . . . Hydrogenation of xylose to xylitol is carried out in aqueous solution, usually at basic pH, with Raney nickel catalyst at a loading of 2%, at 125° C. and 3.5 MPa (515 psi)," An alternative aqueous crystallization process is described in U.S. Pat. No. 3,985,515 to Jaffe et al.

Xylitol produced in this fashion is typically moisture sensitive and is thus prone to caking, making it difficult to use such product after periods of storage due to the clumping that typically occurs. When xylitol powder is employed in sucrose free chewing gum, where it is used as part of the sweetner/bulking agent as a replacement for sugar, manufacturers may typically bring in xylitol crystallized from solution in bulk, unground form then grind it down themselves, just prior to addition to the gum batch, in order to minimize caking and the problems associated therewith.

Moreover, due to its crystalline structure, i.e., distinct single crystal, definitive form, and very dense nature, when added to gum, aqueous crystallized xylitol does not "dry" the gum out and even with reductions in plasticizer, the gum is typically very soft and difficult to handle/process in gum plants and the gum produced has a coarse texture. At the typical use levels of 7–15% (based on total weight), gum containing aqueous crystallized xylitol poses unique handling problems.

Another characteristic of the single crystalline form of aqueous crystallized xylitol is that such structure does not allow for any "copenetration" of the crystals to effect a bond of the crystals during the preparation of a dried compression tablet. The dense nature of the crystal results in crystals with very low plastic deformation characteristics or values and the bonding energy of the crystal is low. As a result, it is not possible to make a direct compression tablet having an acceptable degree of hardness and texture from xylitol powder produced from an aqueous crystallization process. Rather, one must first wet the xylitol powder with water in a high velocity air stream to form an agglomerate, and then dry and size the resulting product. Product produced by this process can be used in direct compression applications to make tablets of good hardness and durability. It is an added expense however to have to agglomerate the product from the ground aequeous crystallized xylitol. The added expense plus the "grittiness" that is acquired in the agglomeration process has greatly limited the use of xylitol as an excipient for tablet manufacture.

Accordingly, it would be greatly desirable to produce a novel form of crystalline xylitol which, when ground to a powder, exhibited increased moisture resistance and correspondingly less of a tendency to cake. It would further be greatly desirable to process a novel form of crystalline xylitol which had a unique crystalline habit or a less dense crystalline structure such that it could easily be formulated into or directly compressed into tablets without requiring an intervening agglomeration and grinding step, or formulated into chewing gum having reduced grittiness and tackiness.

Accordingly, it is an object of this invention to provide a novel crystalline form of xylitol having increased resistance to moisture pickup.

It is a further object of this invention to provide a novel form of crystalline xylitol which can be more easily formulated into chewing gum.

It is yet another object of this invention to provide a crystalline xylitol which can be directly compressed into tablets having an acceptable degree of hardness without the need for an intermediate agglomeration step.

It is yet a further object of this invention to provide a method of producing such a novel form of xylitol.

These objects and other additional objects will become more fully apparent from the following description and accompanying Examples.

SUMMARY OF THE INVENTION

In one aspect, this invention is directed to melt crystallized xylitol characterized by:
(a) an agglomerated crystal structure having a plurality of crystals making up the individual granules as examined under a scanning election microscope at 2000× power;
(b) a surface area of at least about 0.12 square meters per gram; and
(c) a Strong Cobb Arner hardness value of at least about 6 when compressed into a round, flat, beveled edge tablet which is ½ inch in diameter and which is formed under 3.2 tons pressure on a 1.00±0.05 gram charge consisting of 99.5% by weight of a −40/+200 mesh powder of the crystalline xylitol and 0.5% by weight of magnesium stearate.

In another aspect, this invention is directed to a process for producing melt crystallized xylitol, which process comprises the steps:
(a) forming molten xylitol by heating xylitol above its melting point;
(b) cooling such molten mixture under agitation until a viscous mass is formed; and
(c) cooling such viscous mass slowly until the xylitol becomes fully crystallized.

In other aspects, this invention is directed to ingestible compositions such as chewing gum, tablets and the like comprising such melt crystallized xylitol.

DETAILED DESCRIPTION OF THE INVENTION

The melt crystallized xylitol of this invention is characterized by:
(a) an agglomerated crystal structure having a plurality of crystals making up the individual granules as examined under a scanning election microscope at 2000× power;
(b) a surface area of at least about 0.12 square meters per gram; and
(c) a Strong Cobb Arner hardness value of at least about 6 when compressed into a round, flat, beveled edge tablet which is ⅜ inch in diameter and which is formed under 3.2 tons pressure on a 1.00±0.05 gram charge consisting of 99.5% by weight of a −40/+200 mesh powder of the crystalline xylitol and 0.5% by weight of magnesium stearate.

Figure 1A:
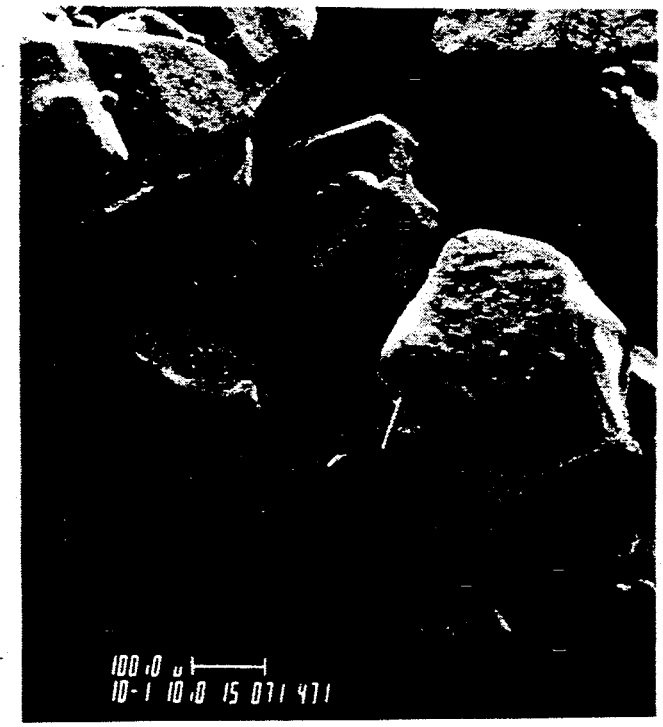
FIGS. 1a and 1b depict typical scanning electron photomicrographs of aqueous crystallized xylitol, the Figures being at 100× and 2000× magnification, respectively.
Figure 1B:
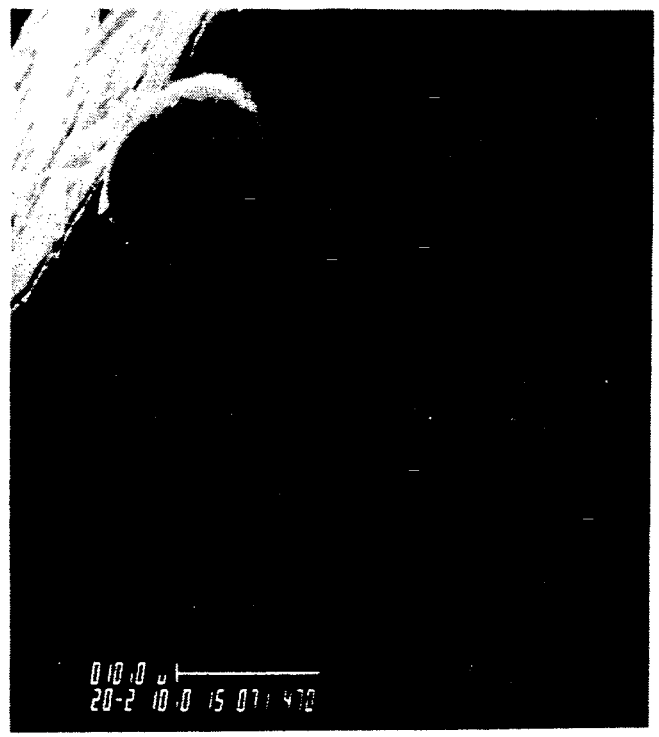
Figure 2A:
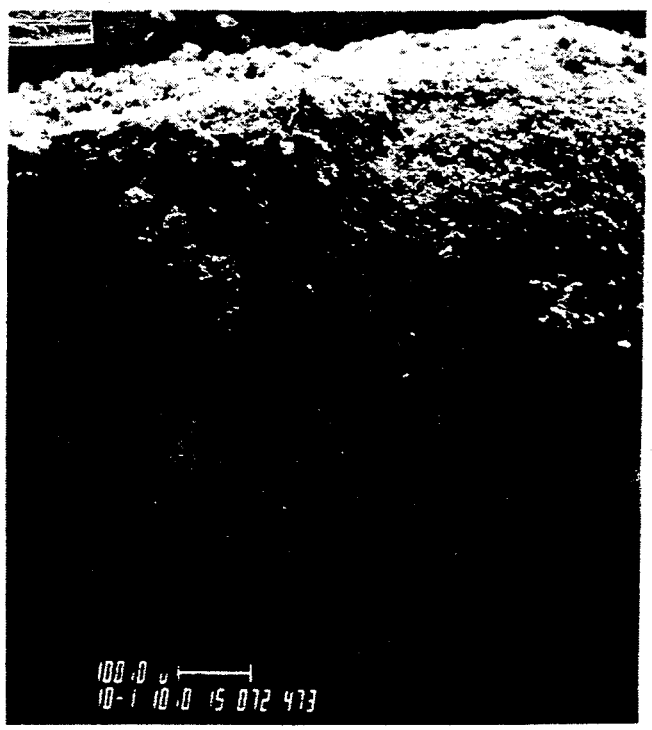
FIGS. 2a and 2b depict typical scanning electron photomicrographs of the melt crystallized xylitol of the invention, the Figures being at 100× and 2000× magnification, respectively.
Figure 2B:

The agglomerated crystal structure of the melt crystallized xylitol of this invention is clearly shown in FIGS. 2a and 2b wherein it is seen that such product is characterized by a number of crystals making up the individual granules. In contrast, the scanning electron microscope pictures of commercially available aqueous crystallized xylitol presented in FIGS. 1a and 1b show that such material is characterized by a single very dense crystal. It is believed that this composite crystal structure of the melt crystallized xylitol granule results in such material having a "porosity" and thus different physical properties.

Among the more important properties found to be exhibited by the melt crystallized xylitol of this invention is its ability to be directly compressed into tablets having an acceptable hardness. When compressed into round, flat, beveled edge tablets which are ⅜ inch in diameter and which are formed under 3.2 tons pressure on a 1.00±0.05 gram charge consisting of 99.5% by weight of a −40/+200 mesh powder of xylitol powder and 0.5% by weight of magnesium stearate, the melt crystallized xylitol of this invention will typically exhibit a Strong Cobb Arner hardness value of at least about 6, preferably of at least about 9, and most preferably of at least about 12. In contrast, aqueous crystallized xylitol of the same mesh size (i.e. small enough to pass through a 40 mesh screen but too large to pass through a 200 mesh screen) will typically only produce a tablet having a Strong Cobb Arner value of less than 5 under such conditions.

The melt crystallized xylitol of this invention is further typically characterized by a surface area of at least about 0.12 square meters per gram, preferably of at least about 0.14 square meters per gram and most preferably of at least about 0.16 square meters per gram. This increased surface area (which is typically more than twice the surface area of aqueous crystallized xylitol) is believed to arise from the agglomerated structure of the melt crystallized xylitol particles.

In this regard, one particularly unexpected advantage of the melt crystallized xylitol of this invention is that, despite its increased surface area (it has been found that in certain circumstances when aqueous crystallized xylitol has been reprocessed into melt crystallized xylitol that the surface area increased almost three times) such material exhibits increased resistance to moisture pickup. Accordingly, melt crystallized xylitol is much less prone to caking then is aqueous crystallized xylitol, with the result that onsite grinding steps may be avoided.

A second unexpected property of the melt crystalline xylitol of this invention is such product's ability to be more easily formulated into products such as chewing gums. Thus, as is shown in the Examples following, the use of melt crystalline xylitol in standard gum formulations tends to dry out the gum such that it is more easily rolled and scored. In contrast, the use of equal amounts of aqueous crystallized xylitol of the same particle size distribution results in the production of a chewing gum which is much stickier and difficult to roll and score. Moreover, the gum produced using the melt crystallized xylitol is much less grittier.

These properties result in melt crystallized xylitol having a number of unexpected advantages relative to aqueous crystallized xylitol when formulated into ingestible confectionary and/or medicinal compositions, including chewing gym, tablets and the like. Such confectionary and/or medicinal compositions may be formulated as would be apparent to one of ordinary skill employing melt crystallized xylitol as the starting material in place of other hexitol and/or pentatol dervied products.

The xylitol of this invention may be produced by the steps of:
(a) forming molten xylitol by heating xylitol above its melting point;
(b) cooling such molten mixture under agitation until a viscous mass is formed; and
(c) cooling such viscous mass slowly until the xylitol becomes fully crystallized.

In general, the microcrystalline xylitol product of the invention is made by dehydrating a purified aqueous solution of xylitol to a solids content of at least about 98 percent and preferably of at least about 99.5 percent. The dehydrated product is then heated to form a clear liquid molten material at a temperature in the range of about between about 121° C. and about 126° C.

The temperature of the molten xylitol is then reduced while agitation continues. Such cooling with agitation results in the onset of crystallization. Agitation should be continued until the formulation becomes a viscous mass. By the term "viscous mass" is meant a composition which has a semi-solid, dough-like appearance: is extrudable; and is not liquid and runny. Typically, at this point the xylitol is generally at least about 60 percent crystalline by weight. If desired, the molten mass of xylitol may be periodically monitored, e.g., by differential scanning calorimetry, until the required percentage crystallinity (which percentage can easily be determined by running trials at various times until a suitable viscous mass is formed and then determining the crystallinity of such viscous mass, e.g. by differential scanning calorimetry) is observed.

The viscous mass is removed from the agitating means and allowed to further cool until a solid crystalline mass is formed. Although the molten mass can fully crystallize under agitation, this is generally not preferred as such solid material may block up the crystallizer and even damage the agitation means employed.

The fully crystalline mass may be ground, employing conventional grinding equipment, to provide a powder which can be formed into tablets or blended with additional excipients and formulated into chewing gums, tablets, and the like.

Large scale preparations may preferably be made employing a process wherein the molten xylitol is heated to a temperature of between about 140° C. and about 150° C. and subjected to agitation in a heated tank. The reaction mass is metered into a continuous twin shaft mixer of the intermeshing type. Mixers of this type are discussed in "Chemical Engineers Handbook", 5th Edition, edited by R. H. Perry and C. H. Chilton (1973) pages 19–21. Characteristics of these mixers are that they include intermeshing kneader blades mounted on two parallel shafts which rotate in the same direction at the same speed with close blade-to-wall and blade-to-blade clearances.

A preferred continuous mixer is the high shear Readco Continuous Processor made by Teledyne Readco of York, Pa. The mixer shown U.S. Pat. No. 3,419,250 and in U.S. Pat. No. 3,618,902 (both assigned to Teledyne Inc.) can be used without modification; however, the viscous xylitol mass which is formed in the present process is much more easily handled if the mixer is equipped with an extrusion nozzle or plate. Other high shear continuous twin screw mixers which impart a high shearing force at low shaft speed to the material being processed can also be used. Such mixers include the Baker, Perkins Multi-Purpose (M-P) mixer made by Baker, Perkins Inc. of Saginaw, Mich., and the ZSK Twin Screw Compounding Extruder made by Werner and Pfleiderer Corporation of Stuttgart, Germany. The Baker, Perkins mixer is shown in U.S. Pat. Nos. 3,195,868 and 3,198,491. Alternative blade configurations can be used in mixers of this type are shown in U.S. Pat. Nos. 3,423,074 (assigned to Baker, Perkins) and 3,490,750 (assigned to Teledyne, Inc.). These mixers are available in various diameters and horse power ratings depending on the throughput required.

Preferably, a Readco Continuous Processor with kneader blade diameters of 5, 15 or 24 inches with feed and/or discharge screws is utilized. Further, the discharge nozzles are preferably provided with heating means in order that the surface of the partially solidified cylindrical ribbon of exiting magma does not prematurely crystallize ensuring a smooth discharge. Thus, one process for producing the melt crystallized xylitol of this invention involves continuously introducing a feed comprising the molten magma into an elongated mixing zone having shaft means and a plurality of kneader blades mounted on the shaft means, the configuration of the kneader blades being such as to provide restricted clearances between the blades and the adjacent walls; simultaneously cooling and kneading the molten xylitol magma as it passes through the mixing zone until a viscous mass of molten xylitol is obtained; and continuously discharging the blend from the mixing zone through an extrusion orifice and further cooling the blend to ambient temperature forming the melt crystallized xylitol.

In carrying out the crystallization, the molten xylitol is preferably held in an agitated feed tank in a relatively dry atmosphere to inhibit moisture pickup such that the moisture content does not exceed about 1% by weight. In the operation of the mixing equipment, the feed rate and other operating parameters are adjusted such that as the cooling mass passes through the mixer, a molten blend having increased concentrations of crystals is generated as the magma passes through from the feed to the discharge orifice. The rotating screws move the molten magma from the center of the equipment to the outer cooled edge whereupon crystals are precipitated and remixed with the molten alcohol. As the temperature profile drops from molten feed temperature to discharge temperature, the viscosity of melt increases due to the formation of the crystals. The action of the rotating screws pushes the crystallizing molten magma in the form of extrudate through the discharge orifice whereupon it is extruded as an elongated mass. The extrudate may then be conveniently cut into desired lengths and permitted to cool until crystallization is complete.

Care should be taken to ensure that the temperature of the emitted extrudate is not too hot, as the molten mass will lose its shape. Not only is such material difficult to handle, but the product obtained may be an undesirable mixture of crystals and amorphous glass. The problem can be corrected by decreasing the throughput time or jacket cooling temperature and other variables such as feed temperature, rotation speed, back pressure, etc. Under ideal operating conditions, the extrudate crystalline paste develops a solid outer shell of crystalline product which is only slightly wetter on the interior side with molten material. The hot extrudate when permitted to stand will fully crystallize, typically over a period of between about 6 hours or less and about 96 hours or more depending on the cross-sectional dimension of the extrudate mass (which typically ranges in cross-section from about 5 to about 20 millimeters). Longer periods may be required for extruded shapes having a cross-sectional dimension of greater than 20 millimeters.

EXAMPLES

The following Examples are intended to further illustrate the invention and are not intended to limit the scope of the invention in any matter whatsoever. In such Examples, all proportions expressed are by weight unless otherwise specified.

EXAMPLE 1

A laboratory apparatus comprising a 500 milliliter boiling flask was submersed in a water bath placed on a hot plate. Into this boiling flask was inserted a polytetrafluoroethylene agitator blade 2 inches in length which was attached to a high speed motor capable of turning the blade in excess of 250 r.p.m. when operated at high speed. A thermometer was placed in a boiling flask as well as the water bath to monitor temperatures.

A 70% solution of xylitol was cooked to about 170° C. on an electric hot place equipped with a magnetic stirrer. Care was taken to boil the solution as rapidly as possible to prevent anhydrization of the molecule. Upon obtaining 170° C., the xylitol melt was placed in the boiling flask, which was immersed in 80° C. water. The xylitol melt was allowed to equilibrate at 92° C. for a period of 20 minutes while being stirred with the agitator set at 100 r.p.m. After 20 minutes when the xylitol reached equilibrium in temperature with the 90° C. water bath, agitation was increased to 250 r.p.m. with 1 gram of finely ground xylitol seed crystal being added to the vortex of the agitating melt.

The seeded melt was allowed to mix at high speed for 38 minutes, at which time it was noticeably more viscous due to crystal formation. At this time the melt was poured onto an aluminum foil covered tray and within 15 minutes after pouring, the mass had totally crystallized into a white solid.

In carrying out the melt crystallization of xylitol in this manner, it appears that the melt must be dehydrated to a point containing less than 2% moisture, and that the xylitol melt must be kept under a high agitation during seeding at 90° C. until crystallization is at least 50% complete.

EXAMPLE 2 AND COMPARATIVE EXPERIMENT A

A portion of the solidified crystalline mass produced in Example 1 was broken up and ground down using a Waring blender using high speed and further screened through a $-40/+200$ (U.S. Sieve Series) screen configuration. The ground/screened material had a less gritty mouth feel than xylitol precipitated from an aqueous solution.

Tablets were made from a blend containing 99.5 parts of the $-40/+200$ screened material mixed with 0.5 parts magnesium stearate. Such tableting was accomplished employing a commercially available Stokes B-2 Press using ⅜" FFBE punches under 3.2 tons of pressure. A 1.0 gram tablet was produced with excellent hardness of at least 12 kilograms (Kg) when tested in a Strong Cobb Arner hardness tester. A comparable tablet made with aqueous crystallized xylitol had a hardness value of less than 5 Kg.

EXAMPLE 3 AND COMPARATIVE EXPERIMENT B

A sample of melt crystallized xylitol produced as described in Example 1 was ground in a Waring blender and passed through a 40 mesh stainless steel screen. This sample was then formulated into a chewing gum by blending with those components described below in Table I, wherein all components are listed in grams.

As a comparison, a similar mesh size commercially available aqueous crystallized xylitol (Comparative Experiment B) was similarly formulated.

TABLE I

| Component | Example 3 | Comparative Experiment B |
|---|---|---|
| Gum base | 25 | 25 |
| Crystalline sorbitol | 54 | 54 |
| Melt crystallized xylitol | 15 | 0 |
| Aqueous crystallized xylitol | 0 | 15 |
| Sorbitol 70° solution | 19.5 | 19.5 |
| Glycerine | 0.5 | 0.5 |
| Spearmint | 1.0 | 1.0 |

The formulation of Example 3 was easily rolled out and scored, and produced a gum which was not gritty. In contrast, the formulation of Comparative Experiment B was very sticky and thus difficult to roll out and score, and produced a very gritty gum.

EXAMPLE 4

Molten xylitol was fed into a Readco mixer having counter-rotating mixing blades 5 inches in diameter. The mixer, jacketed with cooling oil at 16° C., was fed at a rate of 240 pounds per hour at a blade rotation speed of 60 revolutions per minute. The exiting material passed through a nozzle at a temperature of 88°-90° C., and was then permitted to cool to room temperature.

The resultant product was found to have a surface area of between about 0.16 and about 0.20 square meters per gram, in contrast to the aqueous crystallized starting material (used to form the molten xylitol) which had a surface area of about 0.05-0.07 m²/g.

The melt crystallized product was determined to have a heat of fusion of 52.4-52.65 calories/gram and a melting point of 93.36°-93.87° C. as determined by differential scanning calorimetry.

EXAMPLE 5 AND COMPARATIVE EXPERIMENT C

A sample of melt crystallized xylitol produced in accordance with the process of Example 4, was ground in a Waring Blender and a $-40/+200$ mesh screened sample obtained. A similarly sized sample (Comparative Experiment C) of aqueous crystallized xylitol was similarly prepared.

Both samples were stored at a temperature of 70° F. and at 70° relative humidity, and the moisture pickup (as percent increase in weight) measured. The results of such testing are summarized in Table II below:

TABLE II

| | Total Percent Water Pickup | |
|---|---|---|
| Day | Example 5 | Comparative Exeriment C |
| 1 | 4.3 | 6.3 |
| 2 | 6.1 | 9.6 |
| 3 | 10.2 | 14.4 |
| 4 | 16.6 | 23.8 |

The reduced extent of water pickup exhibited by the melt crystallized xylitol relative to the aqueous crystallized material is especially unexpected in light of the much larger surface area of the melt crystallized material.

What is claimed is:

1. Melt crystallized xylitol characterized by:
   a) an agglomerated crystal structure having a plurality of crystals making up the individual granules as examined under a scanning electron microscope at 2000× power;
   b) a surface area of at least about 0.12 square meters per gram; and
   c) a Strong Cobb Arner hardness value of at least about 6 when compressed into a round flat beveled edge tablet which is ⅜ inch in diameter and which is formed under 3.2 tons pressure on a 1.00±0.05 gram charge consisting of 99.5% by weight of a $-40/+200$ mesh powder of the crystalline xylitol and 0.5% by weight of magnesium stearate.

2. Melt crystallized xylitol in accordance with claim 1 wherein the surface area is at least about 0.14 square meters per gram.

3. Melt crystallized xylitol in accordance with claim 2 wherein the surface area is at least about 0.16 square meters per gram.

4. Melt crystallized xylitol in accordance with claim 1 wherein the Strong Cobb Arner hardness valve is at least about 9.

5. Melt crystallized xylitol in accordance with claim 4 wherein the Strong Cobb Arner hardness value is at least about 12.

6. An ingestible composition comprising the melt crystallized xylitol of claim 1.

7. An ingestible composition in accordance with claim 6 wherein said ingestible composition is a tablet.

8. An ingestible composition in accordance with claim 6 wherein said ingestible composition is a chewing gum.

* * * * *